US010041952B2

(12) United States Patent
Lim et al.

(10) Patent No.: US 10,041,952 B2
(45) Date of Patent: Aug. 7, 2018

(54) COMPOSITION FOR DETECTING PROTEINS CONTAINING TYROSINE OXIDE-COUPLED BIOMATERIAL

(75) Inventors: Kook Jin Lim, Seoul (KR); Jin Ik Lim, Seoul (KR); Bum Joon Kim, Seoul (KR); Kyung Hwa Yoo, Seoul (KR); Soo Jung Park, Seoul (KR)

(73) Assignee: PROTEOMETECH INC., Seoul (KR)

( * ) Notice: Subject to any disclaimer, the term of this patent is extended or adjusted under 35 U.S.C. 154(b) by 1068 days.

(21) Appl. No.: 13/981,037

(22) PCT Filed: Jan. 20, 2012

(86) PCT No.: PCT/KR2012/000560
§ 371 (c)(1),
(2), (4) Date: Jul. 22, 2013

(87) PCT Pub. No.: WO2012/102535
PCT Pub. Date: Aug. 2, 2012

(65) Prior Publication Data
US 2013/0302911 A1    Nov. 14, 2013

(30) Foreign Application Priority Data

Jan. 26, 2011 (KR) .................. 10-2011-0007969

(51) Int. Cl.
*G01N 33/58* (2006.01)
(52) U.S. Cl.
CPC .................. *G01N 33/583* (2013.01)
(58) Field of Classification Search
None
See application file for complete search history.

(56) References Cited

U.S. PATENT DOCUMENTS

| | | | | |
|---|---|---|---|---|
| 4,806,344 A | * | 2/1989 | Gaskin | A61K 8/20 424/59 |
| 5,561,045 A | * | 10/1996 | Dorval | G01N 33/54306 422/400 |
| 7,217,410 B2 | | 5/2007 | Suslick | |
| 2009/0269733 A1 | | 10/2009 | Khan | |
| 2010/0111871 A1 | * | 5/2010 | Gambhir | A61B 5/0059 424/9.1 |

FOREIGN PATENT DOCUMENTS

| | | |
|---|---|---|
| JP | 1146761 A | 2/1999 |
| KR | 2003-0052688 A | 6/2003 |
| KR | 10-2005-0058431 A | 6/2005 |
| KR | 10-2008-0058964 A | 6/2008 |
| WO | WO1992/018166 A1 | 10/1992 |

OTHER PUBLICATIONS

Glover, SD et al., "Photochemical Tyrosine Oxidation in the Structurally Well-Defined α3Y Protein: Proton-Coupled Electron Transfer and a Long-Lived Tyrosine Radical" Journal of the American Chemical Society (2014) 136:14039-14051.*
International Search Report of PCT/KR2012/000560 dated Sep. 26, 2012.
Eric P. Meyer et al; Three-Dimenstional Reconstruction: A Tissue Embedding Method for Alignment of Serial Sections; Journal of Neuroscience Methods, 26; 1988; pp. 129-132.
Anne B. Groome; Simultaneous Gelatin Embedding of Multiple Areas of the Arterial Tree; Atherosclerosis, 27; 1977; pp. 333-338.
Werner Berens et al. "Different Approaches for Assaying Melanosome Transfer," NIH Public Access Author Manuscript, Pigment Cells Res. Oct. 2005; 18(5): pp. 370-381.
E. Nishimura et al. "introduction of Genes Into Living Cells", Nuclear Instruments & Methods in Physics Research A, 1998, vol. 407, pp. 500-503.
Australian Office Actionfor Patent Application No. 2012209627.
Office action dated Aug. 5, 2014 of the corresponding Chinese Patent Application No. 20128000468.0.

* cited by examiner

*Primary Examiner* — Scott Long
*Assistant Examiner* — Gary E Hollinden
(74) *Attorney, Agent, or Firm* — Lucas & Mercanti, LLP

(57) ABSTRACT

Provided is a composition for detecting a protein, containing a tyrosine oxide-coupled biomaterial. Various diseases may be easily and rapidly diagnosed by easily detecting the composition containing a tyrosine oxide-coupled biomaterial according to the present invention, by identifying a color of the protein bound with a tyrosine oxide-coupled biomaterial prepared by binding tyrosine oxide, which is a natural pigment present in a living body, with the biomaterial. Accordingly, the composition of the present invention may be used to easily and rapidly diagnose various diseases in real time in an operating room, and may usefully replace conventional histological analysis without a secondary antibody reaction and a final operation of color expression.

3 Claims, 2 Drawing Sheets

COMPOSITION FOR DETECTING PROTEINS CONTAINING TYROSINE OXIDE-COUPLED BIOMATERIAL

CROSS REFERENCE TO RELATED APPLICATION

This Application is a 371 of PCT/KR2012/000560 filed on Jan. 20, 2012, which claims the priority of KR Patent Application No. 10-2011-0007969 filed on Jan. 26, 2011, both applications are incorporated herein by reference in their entirety.

FIELD OF THE INVENTION

The present invention relates to a composition for detecting proteins, wherein the composition contains tyrosine oxide-coupled biomaterial.

BACKGROUND OF THE INVENTION

As time progresses, methods of diagnosing various human diseases are being continuously developed. Recently, progress is being made by adopting state-of-the-art imaging techniques in related arts and applying three-dimensional imaging techniques to tissues.

As the most universal and widely used of the methods of diagnosing diseases, histological analysis is used. Since this method is relatively simple and has high reproducibility and accuracy of test results, its targets and necessity have continuously increased. For example, when metastasis of a tumor in a peripheral tissue is distinguished after tumor tissue is removed in an operating room in which tumor surgery is performed, a part of the peripheral tissue is excised to be used to determine whether the tumor is or is not metastasized by histological analysis. Since this method determines whether an obtained sample is or is not metastasized, obtaining suitable tissue is absolutely important, and there is no choice but to depend on the experience of a skilled surgeon. In addition, since the histological analysis includes preparation of a specimen and staining, analysis results cannot be directly obtained in the operating room. Accordingly, development of a method of overcoming the above limits that is capable of easily and rapidly diagnosing a disease in real time is urgently needed.

As a new method of analyzing a living body, a method capable of easily detecting a target without excision of a tissue and several steps of dying and activation, and having high specificity with respect to target cells or bioactive substances, should be needed. A generally and widely used histological analysis includes: dehydrating a tissue which becomes hard by being fixed in a 4-10% (v/v) aldehyde solution for 24 hours with alcohol; immersing the tissue in a paraffin solution melted at 60° C. for 2 hours or more to penetrate paraffin into the tissue or freezing the tissue; forming a sample-resin block in which a sample tissue is well fused with a resin in a refrigerator using a freezable resin; cutting a section having a desired thickness (4-10 μm) with a sharp blade in a microtome, which is a section forming device, to obtain a sample section, and attaching the section to a glass slide; and removing and hydrating the resin; and finally performing several staining methods on the sample section to observe pathologic features (*Journal of Neuroscience Methods*, 26, 2, 1988, pp 129-132; *Atherosclerosis*, 27, 3, 1977, pp 333-338).

However, the histological analysis, which is an invasive analysis used only on an excised tissue, is relatively complicated, and thus is not suitable for rapidly diagnosing a disease. To overcome this problem, many researchers are actively studying direct observation of a tissue in a living body using bio-imaging equipment such as position emission tomography (PET) or computed tomography (CT). However, this equipment is generally diagnostic equipment used before surgery, and is not easily used in an operating room requiring speed. In addition, this equipment has problems regarding biocompatibility of a material and supply of external energy, and therefore it is necessary to develop a more practical bio-imaging technique.

To solve such problems, methods of coloring a quantum dot or fluorescent material-coupled antibody by radiating light thereto have been studied (Korean Patent Nos. 10-877187 and 10-522086 and Korean Patent Publication No. 10-2005-58431). However, the materials disclosed in these references are synthetic metal particles or chemical substances whose stability in a human body has not been proven, and which are thus are only used for in-vitro research.

Accordingly, there is strong demand for developing a method for easily and rapidly diagnosing various diseases in real time, which can solve fundamental problems of bio-imaging techniques, is very safe, can be used in an operating room, and can replace conventional histological analysis.

SUMMARY OF THE INVENTION

The present invention was completed during research by the present inventors into a method capable of replacing conventional histological analysis and easily and rapidly diagnosing various diseases in real time. The inventors confirmed that tyrosine oxide, which is a natural pigment present in a living body, is bound to a biomaterial and then the tyrosine oxide-coupled biomaterial is bound to a protein to allow the color of the protein to be easily ascertained with the naked eye or an optical microscope.

According to an aspect of the present invention, there is provided a composition for detecting a protein, containing a tyrosine oxide-coupled biomaterial.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Figure 1:
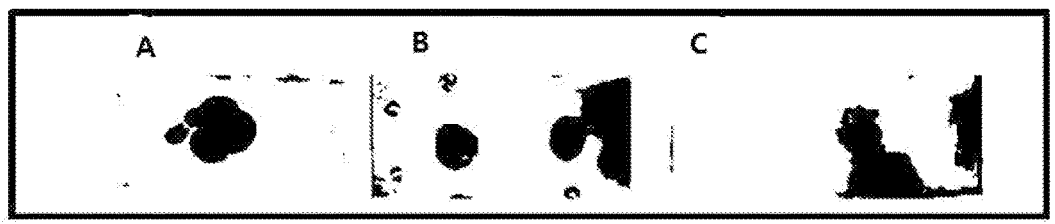
FIG. 1 is a diagram for identifying a color of a protein using a melanin-coupled antibody by a dot blotting method according to the present invention [(A) Example 1, (B) Example 2 and (C) Example 3]

Exemplary embodiments of the present invention will be described in detail below with reference to the accompanying drawings. While the present invention is shown and described in connection with exemplary embodiments thereof, it will be apparent to those skilled in the art that various modifications can be made without departing from the spirit and scope of the invention.

The present invention provides a composition for detecting a protein, containing a tyrosine oxide-coupled biomaterial.

The present invention also provides a method of detecting a protein, including: 1) binding tyrosine oxide to a biomaterial, and 2) binding the tyrosine oxide-coupled biomaterial to a protein and identifying a color of the protein.

Hereinafter, the present invention will be described in detail.

The composition for detecting a protein according to the present invention is prepared by binding tyrosine oxide to a biomaterial.

The tyrosine oxide may be artificial tyrosine oxide obtained by oxidizing tyrosine with a peroxide such as hydrogen peroxide or tyrosinase, or natural tyrosine oxide present in a living body. The tyrosine oxide is a melanin-based compound having a molecular weight of 1000 to 7,000,000 and displaying at least one of black, yellow, orange, purple and red, or a mixed color thereof. The tyrosine oxide includes, but is not limited to, at least one selected from the group consisting of melanin, dopa, dopaquinone, dopacrom, 5,6-dioxindole, 5,6-indolequinone, 5,6-dihydroxyindole (DHI) and 5,6-dihydroxyindole-2-carboxylic acid (DHICA).

The biomaterial includes, but is not limited to, at least one selected from the group consisting of an antibody, a receptor protein, an RNA, a DNA, a peptide nucleic acid (PNA) and an aptamer.

The tyrosine oxide and the biomaterial may be bound to each other by a urethane bond, an ester bond, a peptide bond, hydrophobic adsorption or an ion bond.

The tyrosine oxide-coupled biomaterial may be bound to a protein, and thus a color of the protein may be easily and rapidly identified with the naked eye or an optical microscope. Here, the binding reaction may be performed using a dot blotting method.

As a substrate for a binding reaction between the tyrosine oxide-coupled biomaterial and the protein, a nitrocellulose membrane, a polyvinylidene difluoride (PVDF) membrane, a 96-well plate synthesized with a polyvinyl resin or a polystyrene resin, and a side glass may be used.

As described above, various diseases may be easily and rapidly diagnosed by easily detecting the composition containing a tyrosine oxide-coupled biomaterial according to the present invention by identifying a color of the protein bound with a tyrosine oxide-coupled biomaterial prepared by binding tyrosine oxide, which is a natural pigment present in a living body, with the biomaterial. Accordingly, the composition of the present invention may be used to easily and rapidly diagnose various diseases in real time in an operating room, and may usefully replace conventional histological analysis without a secondary antibody reaction and a final operation of color expression.

Hereinafter, to help with understanding the present invention, Examples will be suggested. The following Examples are merely provided to assist in understanding the present invention, but the scope of the present invention is not limited to the following Examples.

Example 1: Preparation of Tyrosine Oxide-Coupled Antibody 10 mg of melanin, which is tyrosine oxide synthesized using hydrogen peroxide, was dispersed in 700 µl of distilled water, and a carboxyl group of the melanin was activated by reacting 4 mg of 1-ethyl-3-(3-dimethylaminopropyl) carbodiimide hydrochloride (EDC) with 4 mg of N-hydroxysuccinimide (NHS) for 5 minutes. Here, 50 µg of HERCEPTIN® as an antibody was added thereto and reacted for 5 minutes, and 200 µl of 1 M ethanol amine (EA), which was a reaction terminator, was added thereto, thereby preparing a melanin-coupled antibody.

Example 2: Preparation of Tyrosine Oxide-Coupled Antibody

A melanin-coupled antibody was prepared by the same method as described in Example 1, except that melanin isolated from squid ink was used instead of the tyrosine oxide in Example 1.

Example 3: Preparation of Tyrosine Oxide-Coupled Antibody

A melanin-coupled antibody was prepared by the same method as described in Example 1, except that melanin isolated from squid ink and oxidized with hydrogen peroxide for 24 hours and dried was used instead of the tyrosine oxide in Example 2.

Example 4: Preparation of Tyrosine Oxide-Coupled Antibody 20 mg of citraconic anhydride was added to 10 µg/ml of cysteine to block an amine of the cysteine, and carboxyl groups of the cysteine were activated by reacting 4 mg of EDC with 4 mg of NHS for 5 minutes. Here, an antibody-cysteine conjugate was prepared by reacting 50 µg of HERCEPTIN® as an antibody with the above reaction product for 5 minutes. The prepared antibody-cysteine conjugate was mixed with 20 mg of tyrosine, and a tyrosinase was added to be 100 U to oxidize the tyrosine and induce the binding with the cysteine. By the above-described method, an antibody-pheomelanin conjugate was prepared.

Experimental Example 1: Identification of Protein Color Using Tyrosine Oxide-Coupled Antibody: Dot Blotting Method An antibody solution was prepared by adding 100 µl of a 5% skim milk solution to each of the melanin-coupled antibodies prepared in Examples 1 to 3. 0.05 µg/µl of an ERBB2-D1-D4-His solution previously prepared as an antigen was dropped on a nitrocellulose membrane and dried, and the antibody solution was added thereto. After one hour, the nitrocellulose membrane was washed with a PBS buffer solution including 0.05% Tween-20 and observed with the naked eye.

The results are shown in FIG. 1.

As shown in FIG. 1, a melanin-coupled antibody was specifically bound only to a part where the antigen was dropped, and it was seen that the part looked black.

Comparative Experimental Example 1: Identification of Protein Color Using Conventional Secondary Antibody: Dot Blotting Method An antibody solution was prepared by adding 100 µl of a 5% skim milk solution to 50 µg/900 µl of HERCEPTIN® as an antibody. An ERBB2-D1-D4-His solution previously prepared as an antigen was dropped on a nitrocellulose membrane in concentrations [(A) 0.1 ng/µl, (B) 0.025 µg/µl, (C) 0.05 µg/µl, (D) 0.1 µg/µl and (E) 0.2 µg/µl] and dried, and the antibody solution was added thereto. After one hour, goat anti-human IgG-HRP was added as a secondary antibody, shaken for 1 hour and washed. Subsequently, a coloring reagent composed of hydrogen peroxide and 4-chloro-1-naphthol (4CN) as a substrate of a horseradish peroxidase (HRP) was added thereto, shaken for 30 minutes, and observed with the naked eye.

Figure 2:
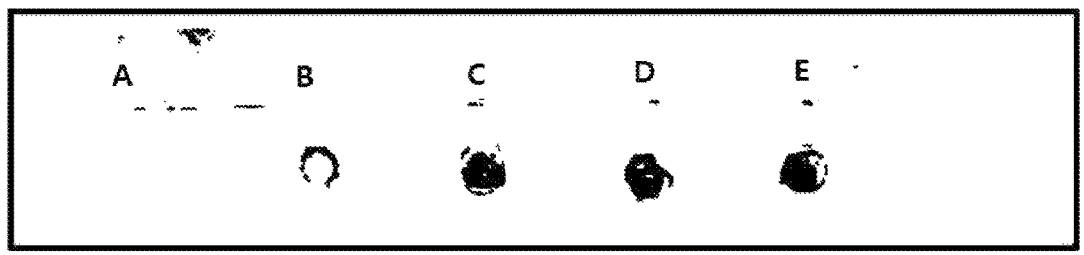
FIG. 2 is a diagram for identifying a color of a protein using a conventional secondary antibody by a dot blotting method, depending on concentration of an antigen [(A) 0.1 ng/μl, (B) 0.025 μg/μl, (C) 0.05 μg/μl, (D) 0.1 μg/μl and (E) 0.2 μg/μl].

The results are shown in FIG. 2.

As shown in FIG. 2, it was seen that a part onto which the antigen was dropped looked black, in proportion to the concentration of the antigen.

The composition for detecting a protein according to the present invention may be used to easily and rapidly diagnose various diseases in real time in an operating room, and may usefully replace conventional histological analysis without a secondary antibody reaction and a final operation of color expression.

Various diseases can be easily and rapidly diagnosed by easily detecting the composition for detecting a protein containing a tyrosine oxide-coupled biomaterial according to the present invention, by identifying a color of the protein bound with a tyrosine oxide-coupled biomaterial prepared by binding tyrosine oxide, a natural pigment present in a living body, with the biomaterial. Accordingly, the composition for detecting a protein of the present invention can be used to easily and rapidly diagnose various diseases in real time in an operating room, and can usefully replace conventional histological analysis without a secondary antibody reaction and a final operation of color expression.

It will be apparent to those skilled in the art that various modifications can be made to the above-described exemplary embodiments of the present invention without departing from the spirit or scope of the invention. Thus, it is intended that the present invention cover all such modifications provided they come within the scope of the appended claims and their equivalents.

What is claimed is:

1. A composition for detecting a protein with a naked eye or an optical microscope, consisting essentially of a tyrosine oxide-coupled biomaterial, wherein
    the tyrosine oxide displays a visible color and is selected from the group consisting of dopa, dopaquinone, dopachrome, 5,6-dioxindole, 5,6-indolequinone, 5,6-dihydroxyindole (DHI) and 5,6-dihydroxyindole-2-carboxylic acid (DHICA); and
    the biomaterial is selected from the group consisting of an antibody, a receptor protein, RNA, DNA, peptide nucleic acid (PNA) and an aptamer.

2. A method of detecting a protein, comprising:
    binding the composition of claim 1 to the protein and identifying said visible color with a naked eye or an optical microscope.

3. The method of claim 2, wherein the tyrosine oxide is coupled to the biomaterial by a bond selected from the group consisting of a urethane bond, an ester bond, a peptide bond, a hydrophobic adsorption and an ion bond.

* * * * *